(12) United States Patent
Pachur et al.

(10) Patent No.: US 8,222,402 B2
(45) Date of Patent: Jul. 17, 2012

(54) PREPARATION PROCESS

(75) Inventors: Kathrin Pachur, Schwendi (DE);
Stefan Goepper, Biberach (DE);
Guenther Huchler, Hochdorf (DE);
Michael Konrad, Biberach (DE);
Kathrin Maier,
Ochsenhausen/Goppertshofen (DE);
Werner Rall, Rheinboellen (DE); **Uwe
Joerg Ries, Biberach (DE); Andreas
Zopf**, Ehingen/Risstissen (DE)

(73) Assignee: **Boehringer Ingelheim International
GmbH**, Ingelheim am Rhein (DE)

( * ) Notice: Subject to any disclaimer, the term of this patent is extended or adjusted under 35 U.S.C. 154(b) by 235 days.

(21) Appl. No.: 12/672,093

(22) PCT Filed: Aug. 12, 2008

(86) PCT No.: PCT/EP2008/060559
§ 371 (c)(1),
(2), (4) Date: Apr. 7, 2010

(87) PCT Pub. No.: WO2009/021942
PCT Pub. Date: Feb. 19, 2009

(65) Prior Publication Data
US 2011/0071286 A1 Mar. 24, 2011

(30) Foreign Application Priority Data

Aug. 13, 2007 (DE) .......................... 10 2007 038 250

(51) Int. Cl.
*C07D 401/14* (2006.01)
*C07D 211/58* (2006.01)
*C07D 401/04* (2006.01)
*C07C 229/42* (2006.01)

(52) U.S. Cl. .................. 540/500; 544/365; 562/438
(58) Field of Classification Search .................. 540/500;
544/365; 562/438
See application file for complete search history.

(56) References Cited

U.S. PATENT DOCUMENTS

| 6,159,964 A | 12/2000 | Ali et al. |
| 2007/0049581 A1 | 3/2007 | Mueller et al. |

FOREIGN PATENT DOCUMENTS

| CA | 2503455 A1 | 5/2004 |
| CA | 2562526 A1 | 10/2005 |
| CA | 2600909 A1 | 9/2006 |
| EP | 0542363 A2 | 5/1993 |
| WO | 2004037810 A1 | 5/2004 |
| WO | 2005100343 A1 | 10/2005 |
| WO | 2006100009 A1 | 9/2006 |

OTHER PUBLICATIONS

Eldred et al.; Orally Active Non-Peptide Fibrinogen Receptor (GpIIb/IIIa) Antagonists: Identification of 4-[4-[4-(Aminoiminomethyl)phenyl]-1-piperaziny1]-1-piperidineacetic Acid as a Long-Acting, Broad-Spectrum Antithrombotic Agent; Journal of Medicinal Chemistry; 1994; No. 37; pp. 3882-3885.
International Search Report, Form PCT/ISA/210, for corresponding PCT/EP2008/060559; date of mailing: Jan. 22, 2009.

*Primary Examiner* — Bruck Kifle
(74) *Attorney, Agent, or Firm* — Michael P. Morris; Alan R. Stempel

(57) ABSTRACT

A process for preparing compounds of the formula (I)

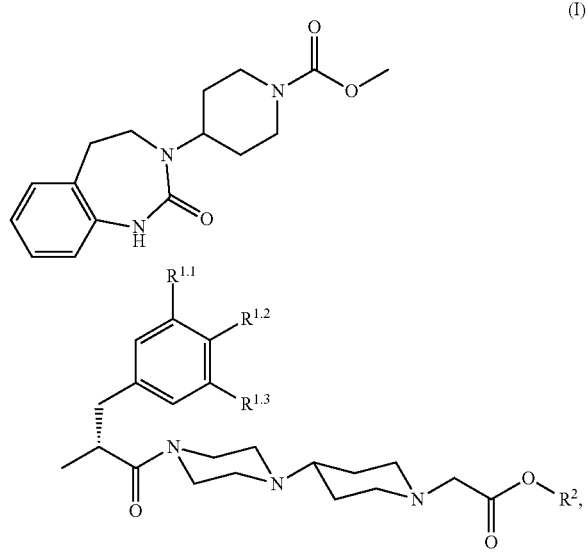

(I)

in which $R^{1.1}$, $R^{1.2}$, $R^{1.3}$ and $R^2$ are as defined in the description.

30 Claims, No Drawings

PREPARATION PROCESS

This application is a national phase entry under 35 U.S.C. 371 of international application PCT/EP2008/060559, filed Aug. 12, 2008, which claims priority to German Application No. 102007038250.4, filed Aug. 13, 2007, each of which is hereby incorporated by reference in its entirety.

The present invention relates to a process for preparing compounds of general formula I

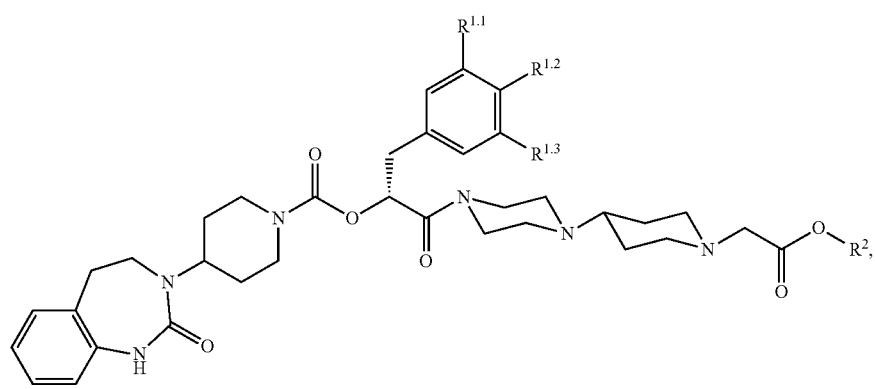

wherein $R^{1.1}$, $R^{1.2}$, $R^{1.3}$ and $R^2$ are defined as mentioned hereinafter, the pharmaceutically acceptable salts thereof and the solvates thereof, which can be prepared starting from compounds of general formula II

BACKGROUND TO THE INVENTION

The present invention relates to a process for preparing compounds of general formula I, which is based on stepwise construction starting from compounds of general formulae III and IV. In addition, the invention relates to the compounds of general formulae III per se, as they are particularly suitable for preparing the compounds of general formula I that have CGRP-antagonistic properties.

DETAILED DESCRIPTION OF THE INVENTION

The compounds of general formulae II and III are valuable starting materials for synthesising the compounds of general formula I which have CGRP-antagonistic properties.

The isolated intermediate stages occur as crystalline solids, which is a major advantage for the purification as well as for separating an mixtures of enantiomers that may occur.

In a first aspect the present invention relates to a process for preparing compounds of general formula II

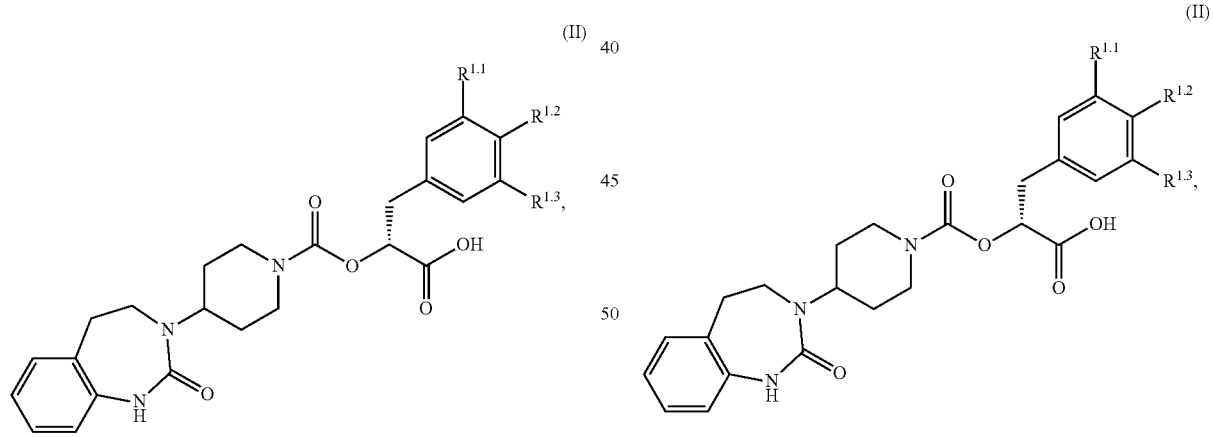

wherein $R^{1.1}$ denotes $CH_3$, $CF_3$, $NR^{1.1.1}R^{1.1.2}$ or piperidinyl,
$R^{1.1.1}$ denotes H, $C_{1-6}$-alkyl, O-benzyl, O-tert.butyl
$R^{1.1.2}$ denotes H, $C_{1-6}$-alkyl, O-benzyl, O-tert.butyl
$R^{1.2}$ denotes $NR^{1.2.1}R^{1.2.2}$,
$R^{1.2.1}$ denotes H, $C_{1-6}$-alkyl, O-benzyl, O-tert.butyl
$R^{1.1.2}$ denotes H, $C_{1-6}$-alkyl, O-benzyl, O-tert.butyl and
$R^{1.3}$ denotes $CH_3$, $CF_3$, F, Cl or Br, comprising the steps of:

wherein $R^{1.1}$, $R^{1.2}$ and $R^{1.3}$ are defined as mentioned hereinafter.

(a) coupling a compound of general formula III

<chemical structure> (III)

wherein $R^{1.1}$, $R^{1.2}$ and $R^{1.3}$ are as hereinbefore defined, with a compound of general formula IV <chemical structure> (IV)

wherein $R^3$ denotes an imidazole or triazole group, preferably an imidazole group which is bound via a nitrogen atom;
(b) isolating the compound of general formula II obtained in step (a) by crystallisation from a solvent and
(c) optionally recrystallising a solid obtained in step (b) from a suitable solvent.

In the coupling in step (a) 1.0 equivalents of a compound of general formula III may be reacted with 1.0 to 1.5 equivalents, preferably with 1.1 equivalents, of a compound of general formula IV in a solvent in the presence of a strong base. The solvent used may be tert.-amylalcohol, tert.-butanol or tetrahydrofuran. The solvent is preferably added in an amount of 2 to 3 L/mol of compound of general formula III used, preferably in an amount of 2.2 to 2.5 L/mol of compound of general formula III used.

The base may be added in an amount of 2.0 to 2.5 equivalents, preferably in an amount of 2.2 equivalents, in each case based on the amount of compound of general formula III used. It is possible to use potassium tert.butoxide, sodium-tert.butoxide, lithium-tert.butoxide or sodium-tert.amylate, while potassium tert.butoxide is preferably used according to the invention.

The crystallisation in step (b) and the recrystallisation in step (c) may be carried out independently of one another in a polar solvent. The polar solvent used may be for example water, acetone, ethanol, isopropanol or n-butyl acetate as well as mixtures of these solvents. According to the invention the crystallisation in step (b) is preferably carried out from a mixture of acetone and water in the ratio 1:1.

In a second aspect the present invention relates to a process for preparing compounds of general formula I <chemical structure> (I)

wherein $R^{1.1}$ denotes $CH_3$, $CF_3$, $NR^{1.1.1}R^{1.1.2}$ or piperidinyl,
$R^{1.1.1}$ denotes H, $C_{1-6}$-alkyl, O-benzyl, O-tert.butyl
$R^{1.1.2}$ denotes H, $C_{1-6}$-alkyl, O-benzyl, O-tert.butyl
$R^{1.2}$ denotes $NR^{1.2.1}R^{1.2.2}$,
$R^{1.2.1}$ denotes H, $C_{1-6}$-alkyl, O-benzyl, O-tert.butyl
$R^{1.2.2}$ denotes H, $C_{1-6}$-alkyl, O-benzyl, O-tert.butyl
$R^{1.3}$ denotes $CH_3$, $CF_3$, F, Cl or Br and
$R^2$ denotes $C_{1-6}$-alkyl,
comprising the steps of:

(a) coupling a compound of general formula III

<chemical structure> (III)

wherein $R^{1.1}$, $R^{1.2}$ and $R^{1.3}$ are as hereinbefore defined, with a compound of general formula IV

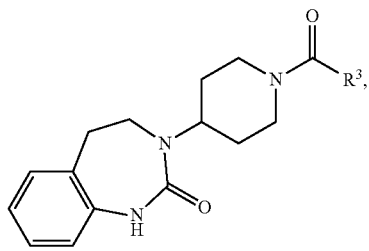

(IV)

wherein $R^3$ denotes an imidazole or triazole group, preferably an imidazole group which is bound via a nitrogen atom;
(b) reacting a product of general formula II

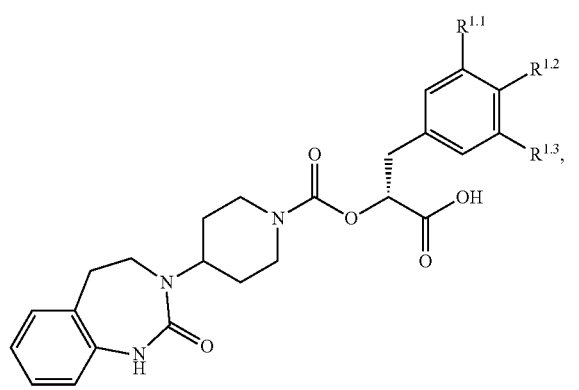

(II)

formed in step (a), wherein $R^{1.1}$, $R^{1.2}$ and $R^{1.3}$ are as hereinbefore defined, with a compound of general formula V

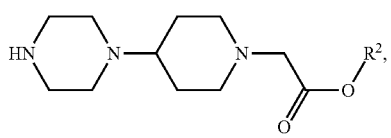

(V)

wherein $R^2$ is as hereinbefore defined; and
(c) optionally recrystallising a solid obtained in step (b) from a suitable solvent.

In the coupling in step (a) 1.0 equivalents of a compound of general formula II and 1.0 to 1.5 equivalents of a compound of general formula III may be suspended in a polar solvent and reacted at elevated temperature in the presence of a strong base.

The polar solvent used may preferably be tert.-amylalcohol, tert.-butanol or tetrahydrofuran. The base used may be selected from among potassium tert.butoxide, sodium-tert.butoxide, lithium-tert.butoxide and sodium-tert.amylate. The reaction is preferably carried out at a temperature between 40° C. and 80° C.

For the reaction in step (b) 1.0 equivalents of a compound of general formula II and 1.1 to 1.5 equivalents of a compound of general formula V may be used. The reaction is preferably carried out at low temperature in the presence of an amine and a condensing agent in a polar solvent.

The amine used may be selected from among triethylamine, diisopropylethylamine, ethyldiisopropylamine and tributylamine and is used in an amount of 5 to 7 equivalents, based on the amount of compound of general formula II used. The condensing agent may be selected from among propanephosphonic anhydride, dicyclohexylcarbodiimide, carbonyldiimidazole, carbonylditriazole, 2-(1H-benzotriazol-1-yl)-1,1,3,3-tetramethyluronium-tetrafluoroborate, 1-ethyl-3-(3'-dimethylamino-propyl)-carbodiimide and chlorodimethoxytriazine, optionally in the presence of hydroxysuccinimide, hydroxybenzotriazole, p-nitrophenol and pentafluorophenol, and is used in an amount of 2 to 3 equivalents, based on the amount of compound of general formula II used.

THF or ethyl acetate may be used as polar solvent.

According to the invention the reaction is preferably carried out at a temperature between 0 and 10° C.

In a third aspect the present invention relates to the compounds of general formula III

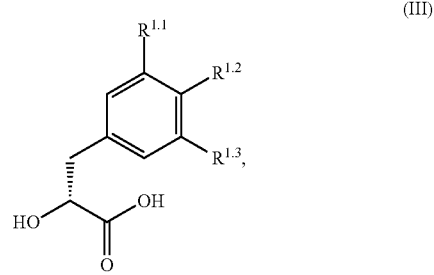

(III)

wherein
$R^{1.1}$ denotes $CH_3$, $CF_3$, $NR^{1.1.1}R^{1.1.2}$ or piperidinyl,
$R^{1.1.1}$ denotes H, $C_{1-6}$-alkyl, O-benzyl, O-tert.butyl
$R^{1.1.2}$ denotes H, $C_{1-6}$-alkyl, O-benzyl, O-tert.butyl
$R^{1.2}$ denotes $NR^{1.2.1}R^{1.2.2}$,
$R^{1.2.1}$ denotes H, $C_{1-6}$-alkyl, O-benzyl, O-tert.butyl
$R^{1.1.2}$ denotes H, $C_{1-6}$-alkyl, O-benzyl, O-tert.butyl
$R^{1.3}$ denotes $CH_3$, $CF_3$, F, Cl or Br and
$R^2$ denotes $C_{1-6}$-alkyl.

A preferred third object encompasses the following compounds of formula IIIa:

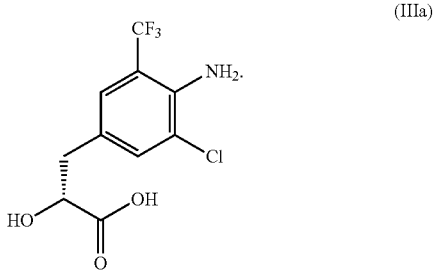

(IIIa)

A more preferred third object relates to the compound (R)-3-(4-amino-3-chloro-5-trifluoromethyl-phenyl]-2-hydroxy-propionic acid of formula IIIa

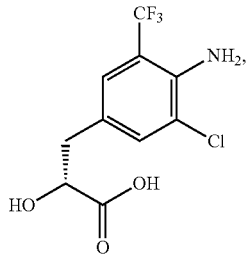

(IIIa)

in crystalline form, which is characterised by a high degree of stability.

The compound of formula IIIa is distinguished by a characteristic melting point of T=141±3° C. The value recorded was determined by Differential Scanning calorimetry (DSC: evaluated by onset, heating rate: 10° C./min) (DSC 821 made by Mettler Toledo).

In another aspect the invention relates to the crystalline compound (R)-3-(4-amino-3-chloro-5-trifluoromethyl-phenyl]-2-hydroxy-propionic acid of formula IIIa, characterised by a melting point of T=141±3° C.

In a fourth aspect the present invention relates to a process for preparing compounds of general formula III

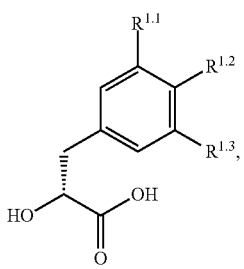

(III)

wherein
$R^{1.1}$ denotes $CH_3$, $CF_3$, $NR^{1.1.1}R^{1.1.2}$ or piperidinyl,
$R^{1.1.1}$ denotes H, $C_{1-6}$-alkyl, O-benzyl, O-tert.butyl
$R^{1.1.2}$ denotes H, $C_{1-6}$-alkyl, O-benzyl, O-tert.butyl
$R^{1.2}$ denotes $NR^{1.2.1}R^{1.2.2}$,
$R^{1.2.1}$ denotes H, $C_{1-6}$-alkyl, O-benzyl, O-tert.butyl
$R^{1.2.2}$ denotes H, $C_{1-6}$-alkyl, O-benzyl, O-tert.butyl and
$R^{1.3}$ denotes $CH_3$, $CF_3$, F, Cl or Br,
comprising the steps of:
(a) reacting a compound of general formula V

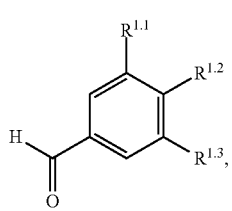

(V)

wherein $R^{1.1}$, $R^{1.2}$ and $R^{1.3}$ are as hereinbefore defined, with a compound of general formula VI

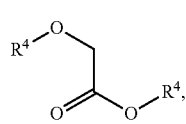

(VI)

wherein $R^4$ independently of one another denotes a $C_{1-6}$-alkyl group, in a solvent and in the presence of a strong base;
(b) cleaving the ester group of a compound of general formula VII

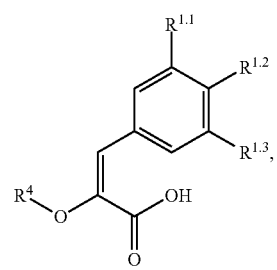

(VII)

obtained in step (a), wherein $R^{1.1}$, $R^{1.2}$ and $R^{1.3}$ are as hereinbefore defined and $R^4$ denotes a $C_{1-6}$-alkyl group, by adding an inorganic base;
(c) optionally isolating a compound of general formula VIII

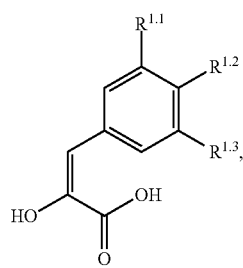

(VIII)

obtained in step (b), wherein $R^{1.1}$, $R^{1.2}$ and $R^{1.3}$ are as hereinbefore defined and $R^4$ denotes a $C_{1-6}$-alkyl group;
(d) cleaving the protective group from a compound of general formula VIII obtained in step (b) or (c) by adding a strong inorganic acid;
(e) optionally isolating a compound of general formula IX (IX)

obtained in step (d), wherein $R^{1.1}$, $R^{1.2}$ and $R^{1.3}$ are as hereinbefore defined;

(f) mixing a compound of general formula IX obtained in step (e) with a solvent and reducing the double bond by adding a reducing agent and in the presence of a base;

(g) isolating a compound of general formula III obtained in step (f) and optionally recrystallising from a solvent.

Another aspect encompasses in step (a) the reaction of a compound of general formula V, wherein $R^{1.1}$ denotes $CF_3$, $R^{1.2}$ denotes $NH_2$, $R^{1.3}$ denotes Cl, with a compound of general formula VI, wherein $R^4$ denotes a methyl group in each case.

In the reaction in step (a), 1.0 equivalents of a compound of general formula V are reacted with 1.8 to 2.5 equivalents, preferably 1.9 to 2.1 equivalents, more preferably 2 equivalents, of a compound of general formula VI.

The solvent used may be tert.-butanol or tetrahydrofuran or mixtures of these solvents. The solvent is added in an amount of 0.5 to 0.8 L/mol, preferably in an amount of 0.6 to 0.7 L/mol of the compound of general formula V used. The base is preferably added in an amount of 1.0 to 1.5 equivalents, preferably in an amount of 1.25 equivalents, based on the amount of compound of general formula V used. It is possible to use potassium tert.butoxide, sodium-tert.butoxide, lithium-tert.butoxide or sodium-tert.amylate, while potassium tert.butoxide is preferably used according to the invention.

Another aspect encompasses in step (b) cleaving the ester group from a compound of general formula VII, wherein $R^{1.1}$ denotes $CF_3$, $R^{1.2}$ denotes $NH_2$, $R^{1.3}$ denotes Cl and $R^4$ denotes $CH_3$.

For the cleaving in step (b) the inorganic base may be selected from among lithium hydroxide, sodium hydroxide and potassium hydroxide. It may be added in an amount of 1.5 to 2.5 equivalents, preferably 2 equivalents, based on the amount of compound of general formula VII used.

The isolation of a compound of general formula VIII described in step (c) may be carried out by crystallisation, for example.

In the cleaving of the protective group described in step (d), 1.0 equivalents of a compound of general formula VIII are reacted with 8 to 12 equivalents, preferably 10 equivalents, of an inorganic acid. The inorganic acid may be selected from among hydrochloric acid, hydrobromic acid, hydriodic acid and sulphuric acid; hydrobromic acid is preferably used.

The solvent mentioned hereinbefore under step (f) may be selected from among n-butyl acetate, isopropyl acetate, ethyl acetate and tetrahydrofuran. The base may be selected from among triethylamine, diisopropylethylamine and pyridine.

The reducing agent also described under step (f) may be selected from among diisopinocampheyl boron chloride, β-chlorodiisopinocampheylborane, Alpine borane and methyl-CBS-oxazaborolidine.

The solvent mentioned hereinbefore under step (g) may be selected from among n-butyl acetate, isopropyl acetate, ethyl acetate and tetrahydrofuran.

Compounds of general formula IV

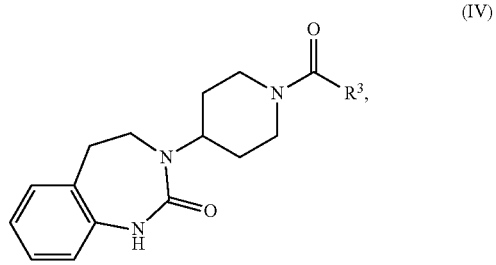

(IV)

wherein $R^3$ denotes an imidazole or triazole group, preferably an imidazole group, which is bound via a nitrogen atom, are prepared by a process comprising the steps of:

(a) reacting carbonyldiimidazole or carbonylditriazole, preferably carbonyldiimidazole, with 1,3,4,5-tetrahydro-3-(4-piperidinyl)-2H-1,3-benzodiazepin-2-one in a polar aprotic solvent at elevated temperature; and (b) crystallising out the crude product formed in step (a) by adding another polar aprotic solvent, if $R^3$ denotes an imidazole group.

The solvent mentioned hereinbefore under step (a) may be selected from among acetone, acetonitrile, tert.butylmethylether, N,N-dimethylacetamide, dimethylformamide, dimethylsulphoxide, pyridine and N-methylpyrrolidone.

The polar, aprotic solvent mentioned hereinbefore under step (b) may be selected from among tert.butylmethylether and dimethylformamide.

In a fifth aspect the present invention relates to a process for preparing compounds of general formula V

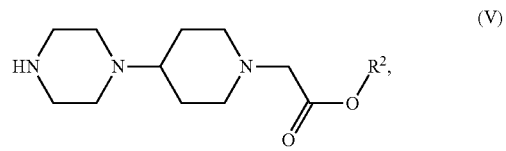

(V)

wherein $R^2$ denotes $C_{1-6}$-alkyl, comprising the steps of:

(a) reacting piperidone-4-hydrate-hydrochloride with a chloroacetic acid ester of general formula X

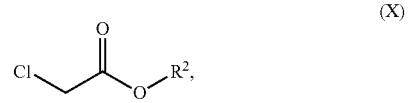

(X)

wherein $R^2$ denotes a $C_{1-6}$-alkyl group, in a solvent and in the presence of a base;

(b) coupling a compound of general formula XI

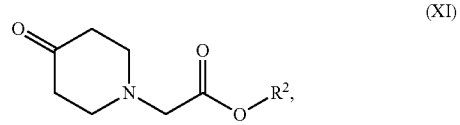

(XI)

obtained under (a), wherein R² is as hereinbefore defined, with 1-benzylpiperidine in a solvent and with the addition of a reducing agent;

(c) reacting a compound of general formula XII

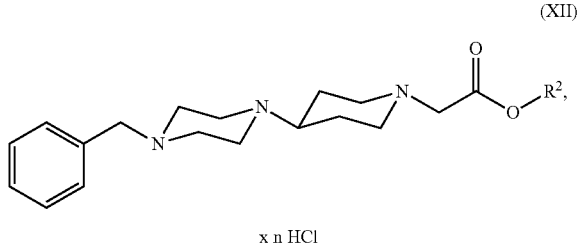

(XII)

x n HCl obtained under (b), wherein R² is as hereinbefore defined and n denotes the number 0, with hydrochloric acid and in a solvent, in order to prepare a compound of general formula XII wherein R² is as hereinbefore defined and n denotes one of the numbers 1, 2 or 3; and (d) cleaving the benzyl protective group from a compound of general formula XII,

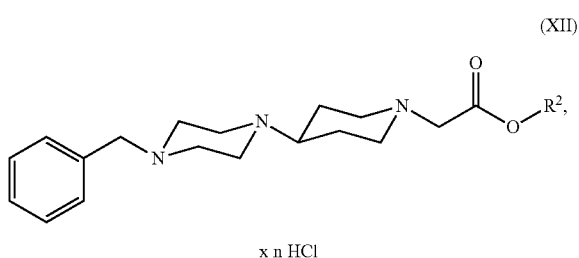

(XII)

x n HCl obtained under (c), wherein R² is as hereinbefore defined and n denotes one of the numbers 1, 2 or 3, in a solvent and in the presence of a catalyst; and (e) isolating a compound of general formula XIII

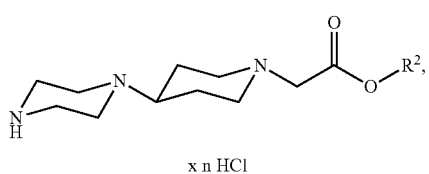

(XIII)

x n HCl prepared under (d), wherein R² is as hereinbefore defined and n denotes one of the numbers 1, 2 or 3.

In the reaction described hereinbefore under step (a) 1.0 equivalents of piperidone-4-hydrate-hydrochloride may be reacted with 1.0 to 1.2 equivalents of a chloroacetic acid ester of general formula X.

The solvent specified may be selected from among acetone, acetonitrile, tert-butylmethylether, N,N-dimethylacetamide, dimethylformamide, dimethylsulphoxide, pyridine and N-methylpyrrolidone, of which acetonitrile is of particular importance. The solvent may be used in an amount of 0.8 to 1.5 L/mol of the piperidone-4-hydrate-hydrochloride used, preferably 0.9 to 1.1 L/mol of the piperidone-4-hydrate-hydrochloride used.

The base may be selected from among sodium carbonate, potassium carbonate, sodium hydride and potassium hydride. It may be added in an amount of 2.0 to 2.5 equivalents, based on the amount of piperidone-4-hydrate-hydrochloride used.

In the coupling described hereinbefore under step (b) 1.0 equivalents of 1-benzyl-piperazine may be reacted with 1.1 to 1.7 equivalents of a compound of general formula XI.

The solvent specified may be selected from among tert-butylmethylether, tetrahydrofuran, toluene and 2-methyltetrahydrofuran. The solvent may be used in an amount of 1.0 to 2.0 L/mol of 1-benzyl-piperazine used.

The reducing agent used may be sodium borohydride or sodium triacetoxyborohydride, which is added in an amount of 1.0 to 2.0 equivalents, based on the amount of 1-benzyl-piperazine used.

the reaction described hereinbefore under step (c) may 1.0 equivalents of a compound of general formula XII may be reacted with 1.1 to 5 equivalents hydrochloric acid.

The solvent specified may be selected from among methanol, ethanol and isopropanol. The solvent may be used in an amount of 2.5 to 4.0 L/mol of 1-benzyl-piperazine used.

The cleaving of a benzyl protective group from a compound of general formula XII described hereinbefore under step (d) may be carried out in a polar solvent, such as for example methanol, ethanol, propanol, tert-butanol, water, acetone, tetrahydrofuran, dimethylformamide or mixtures of these solvents. The solvent may be added in an amount of 4.0 to 7.0 L/mol of compound of general formula XII used.

Advantageous conditions for the hydrogenation are temperatures from 40 to 80° C. and an excess hydrogen pressure of not more than 5 bar. Palladium/charcoal or palladium hydroxide/charcoal may be used as catalyst.

TERMS AND DEFINITIONS USED

Within the scope of this application, in the definition of possible substituents, these may also be represented in the form of a structural formula. If present, an asterisk (*) in the structural formula of the substituent is to be understood as being the linking point to the rest of the molecule.

The subject-matter of this invention also includes the compounds according to the invention, including the salts thereof, wherein one or more hydrogen atoms, for example one, two, three, four or five hydrogen atoms, are replaced by deuterium.

By the term "$C_{1-6}$-alkyl" (including those which are part of other groups) are meant branched and unbranched alkyl groups with 1 to 6 carbon atoms. Examples of these include: methyl, ethyl, n-propyl, iso-propyl, n-butyl, sec-butyl, tert.-butyl, pentyl or hexyl. The abbreviations Me, Et, n-Pr, i-Pr etc. may optionally also be used for the above-mentioned groups.

The compounds of general formula I may have basic groups such as e.g. Amino functions. They may therefore be present as internal salts, as salts with pharmaceutically useable inorganic acids such as for example hydrobromic acid, phosphoric acid, nitric acid, hydrochloric acid, sulphuric acid, methanesulphonic acid, ethanesulphonic acid, benzenesulphonic acid, p-toluenesulphonic acid or organic acids such as for example malic acid, succinic acid, acetic acid, fumaric acid, maleic acid, mandelic acid, lactic acid, tartaric acid or citric acid.

The invention relates to the respective compounds, optionally in the form of the individual optical isomers, mixtures of the individual enantiomers or racemates, in the form of the tautomers as well as in the form of the free bases or the corresponding acid addition salts with pharmacologically acceptable acids.

EXPERIMENTAL SECTION

Example 1

(Z)-3-(4-amino-3-chloro-5-trifluoromethyl-phenyl)-2-methoxy-acrylic acid (C)

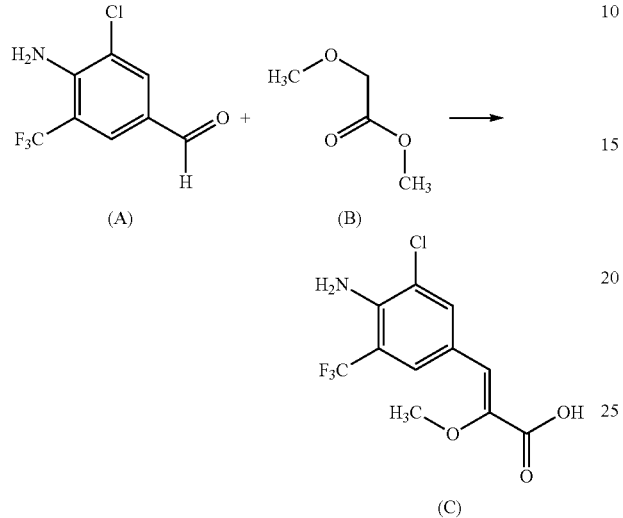

26.14 kg (55.91 mol) potassium tert.butoxide solution in THF were metered into a mixture of 10.00 kg (44.73 mol) 4-amino-3-chloro-5-trifluoromethylbenzaldehyde (A), 9.31 kg (89.45 mol) methyl methoxyacetate (B) and 30.0 L tetrahydrofuran and the mixture was stirred for 24 hours at 20° C. Then 7.16 kg (89.45 mol) sodium hydroxide solution (50%) were metered in and the mixture was heated to 30° C. for 1 hour, before 16.31 kg (134.18 mol) hydrochloric acid (30%) and 15.0 L water were added. After the aqueous phase has been separated off, 40 L of the solvent were distilled off and the residue was combined with 25.0 L toluene, before another 40 L solvent were distilled off. The organic phase was combined with 20.0 L water and cooled to 23° C. After the addition of 10.0 L toluene the suspension was stirred for a further 30 minutes, the product was separated off and dried.

Yield: 10.05 kg (76% of theory)
Melting point: 173° C.

Example 2

(Z)-3-(4-amino-3-chloro-5-trifluoromethyl-phenyl)-2-hydroxy-acrylic acid (D)

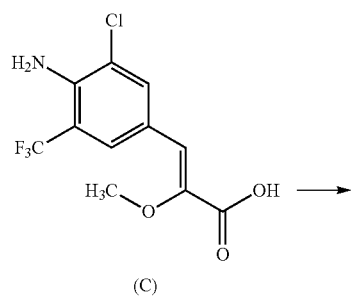

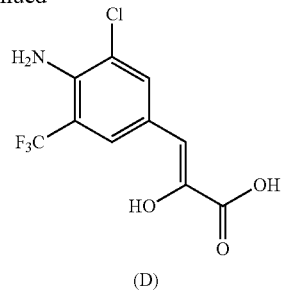

10.00 kg (33.82 mol) (Z)-3-(4-amino-3-chloro-5-trifluoromethyl-phenyl)-2-methoxy-acrylic acid (C) were suspended in 20.0 L acetic acid and heated to 80° C., before 57.02 kg (338.25 mol) hydrobromic acid (48%) were added. Then the reaction mixture was stirred for 1.5 hours at 80° C., then diluted with 78.0 L water and the suspension was cooled to 22° C. The product was separated off, washed with 100.0 L water and dried.

Yield: 9.24 kg (97% of theory)
Melting point: 195° C.

Example 3

(R)-3-(4-amino-3-chloro-5-trifluoromethyl-phenyl]-2-hydroxy-propionic acid (E)

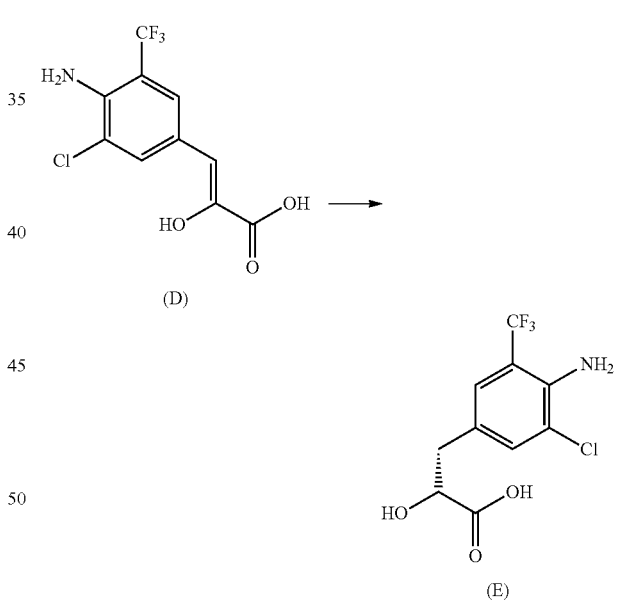

10.00 kg (35.51 mol) (Z)-3-(4-amino-3-chloro-5-trifluoromethyl-phenyl)-2-hydroxy-acrylic acid (D) were suspended in 70.0 L n-butyl acetate, before 22.78 kg (46.16 mol) diisopinocampheyl boron chloride (DIP-chloride, 65% solution in heptane) were metered in at 10° C. Then the reaction mixture was heated to 20° C. and once the reaction was complete 30.0 L water were metered in and the mixture was stirred for another 20 minutes. After the aqueous phase had been separated off the remaining organic phase was extracted first with a mixture of 2.84 kg (35.51 mol) sodium hydroxide solution (50%) and 60.0 L water and then again with 60.0 L water. The two aqueous product phases separated off were combined, diluted with 50.0 L water and 10.0 L solvent were distilled off in vacuo. Then at 60° C. a mixture of 4.53 kg (37.28 mol) hydrochloric acid (30%) and 15 L water was added and the mixture was inoculated with 5.0 g (αR)-α-hydroxy-3 [4-amino-3-chloro-5-trifluoromethyl-phenyl]-propionic acid and cooled to 20° C. The product was separated off, washed with 40.0 L water and dried.

Yield: 7.05 kg (70% of theory) ee value: 95.6%
Melting point: 141° C.

Example 4

(R)-2-(4-amino-3-chloro-5-trifluoromethyl-phenyl]-1-carboxyethyl 4-(2-oxo-1,2,4,5-tetrahydro-1,3-benzodiazepin-3-yl)-piperidine-1-carboxylate (H)

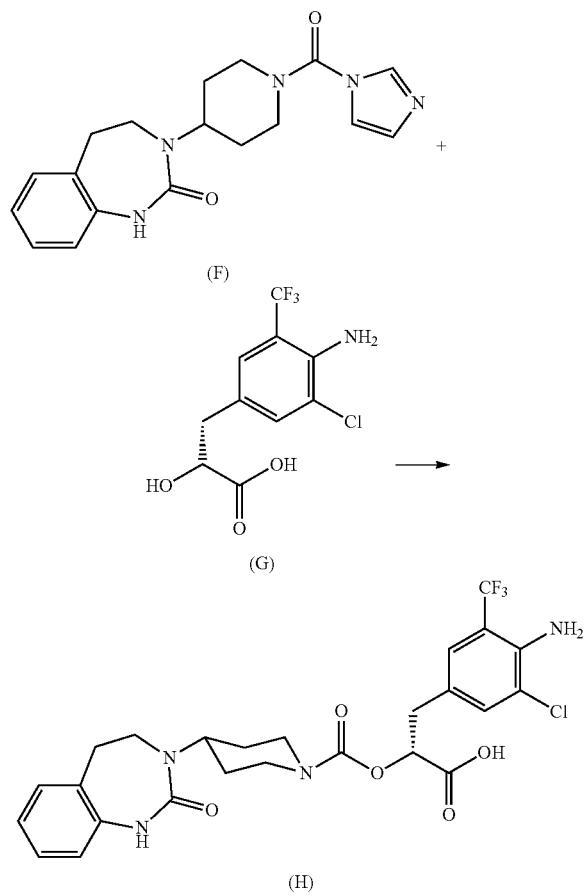

5.00 kg (17.63 mol) (R)-3-(4-amino-3-chloro-5-trifluoromethyl-phenyl]-2-hydroxy-propionic acid (G) and 6.28 kg (19.39 mol) 1-(1H-imidazol-1-yl-carbonyl)-4-(1,2,4,5-tetrahydro-2-oxo-3H-1,3-benzodiazepin-3-yl)-piperidine (F) were suspended in 40.0 L tert.-amylalcohol, before 20 L solvent were distilled off under normal pressure. Then the reaction mixture was cooled to 25° C., 21.76 kg (38.78 mol) potassium tert.butoxide solution in THF was added, before the mixture was heated to 35° C. for 1.5 hours. After the reaction was complete the mixture was cooled to 25° C. cooled and 9.64 kg (79.33 mol) hydrochloric acid (30%), 25.0 L water and 25.0 L acetone were added successively, before the mixture was inoculated with 5 g ethyl (1R)-4-(1,2,4,5-tetrahydro-2-oxo-3H-1,3-benzodiazepin-3-yl)-1-carboxy-2-[4-amino-3-chloro-5-trifluoromethyl-phenyl]-1-piperidinecarboxylate. After stirring overnight the suspension was cooled to 0° C. and stirred for a further hour. The product was separated off, washed twice with 15.0 L water and 15.0 L acetone and dried.

Yield: 8.41 kg (86% of theory)

Example 5

Ethyl (4-oxo-piperidin-1-yl)-acetate (K)

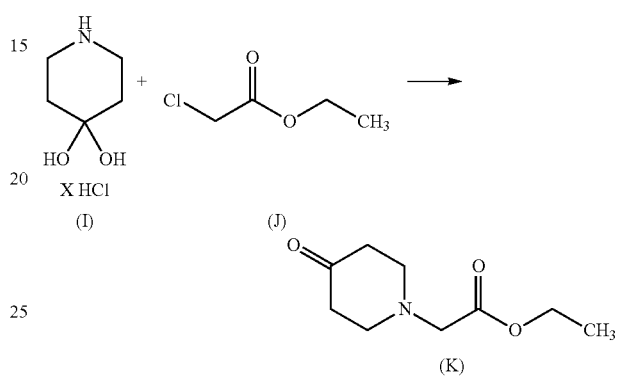

10.00 kg (65.10 mol) piperidone-4-hydrate-hydrochloride (I) were suspended in 66.7 L acetonitrile. After the addition of 19.79 kg (143.22 mol) potassium carbonate the reaction mixture was heated to 75° C. and a mixture of 8.38 kg (68.35 mol) ethyl chloroacetate (J) with 10.0 L acetonitrile was metered in. After the reaction was complete 20.0 L acetonitrile were distilled off and the residue was combined with 50.0 L toluene. Then the suspension was filtered off and the filter cake was washed with 50.0 L toluene before the solvent was distilled off completely in vacuo.

Yield: 11.94 kg (99% of theory)

Example 6

Butyl (4-oxo-piperidin-1-yl)-acetate (M)

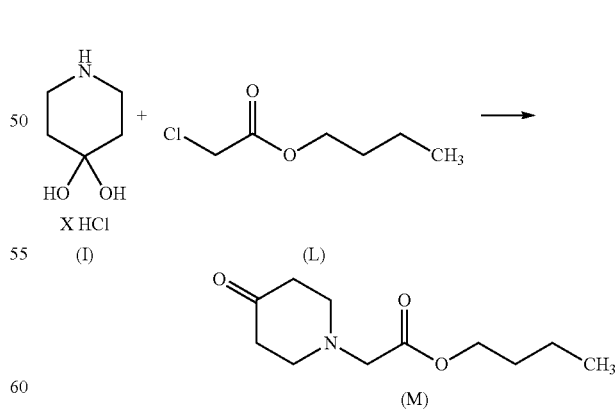

56.1 g (0.36 mol) piperidone-4-hydrate-hydrochloride (I) were suspended in 0.75 L acetonitrile. After the addition of 100 g (0.72 mol) potassium carbonate the reaction mixture was heated to 80° C. and a mixture of 8.38 kg (68.35 mol) butyl chloroacetate (L) with 0.05 L acetonitrile was metered in. Once the reaction was complete acetonitrile was distilled off and the residue was combined with 500 mL ethyl acetate and 500 mL water and stirred. The organic phase was separated off and washed with saturated NaCl solution. After drying on Na₂SO₄ the filtrate was freed from the solvent using the rotary evaporator.

Yield: 71 g (100% of theory)

Example 7

Ethyl [4-(4-benzyl-piperazin-1-yl)-piperidin-1-yl]acetate trihydrochloride (O)

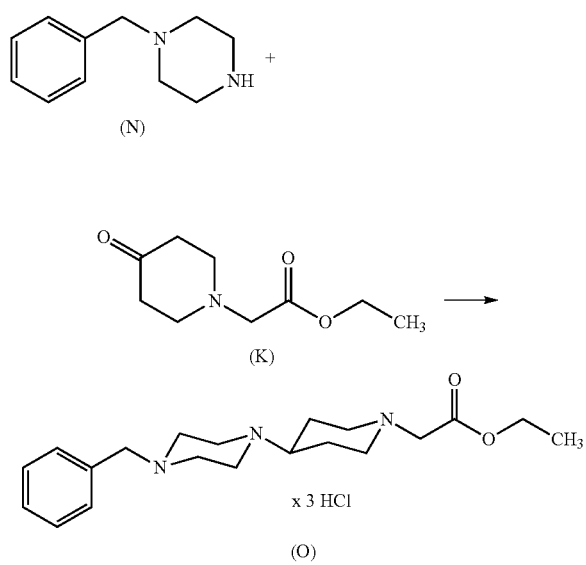

6.85 kg (38.9 mol) 1-benzyl-piperazine (N) were metered into a mixture of 10.00 kg (54.0 mol) ethyl (4-oxo-piperidin-1-yl)-acetate (K), 42 L 2-methyltetrahydrofuran and 11.81 kg (196.7 mol) acetic acid at 20° C. and rinsed with 10.6 L of 2-methyltetrahydrofuran, before the reaction mixture was stirred for one to two hours at 20° C. Then the mixture was metered into the mixture of 12.39 kg (58.5 mol) sodium-triacetoxyborohydride and 36.8 L 2-methyltetrahydrofuran at 20° C., during which time the temperature was allowed to rise to 40° C. After the addition had ended the mixture was rinsed with 15.8 L of 2-methyltetrahydrofuran and the reaction mixture was stirred for at least 1 hour at 40° C. If necessary, further sodium triacetoxyborohydride was added before stirring was continued overnight at 25° C. Once the reaction of the 1-benzylpiperazine was complete the mixture was cooled to 20° C., 52.6 L of water were metered in and the pH was adjusted to 9.0 with 27.3 kg sodium hydroxide solution (50%). After phase separation the organic phase was washed with 26.3 L water and evaporated down completely in vacuo. The residue was taken up in 134 L ethanol and combined with 15.6 kg of 10 molar ethanolic hydrochloric acid (159.4 mol, at least 37.2 wt.-%) at boiling temperature, before the mixture was refluxed for a further 1 hour, with stirring. After cooling to 2° C. and stirring for 1 hour the product was separated off, washed with 31.6 L cold ethanol and dried.

Yield: 16.70 kg (68% of theory)

Example 8

Butyl [4-(4-benzyl-piperazin-1-yl)-piperidin-1-yl]acetate trihydrochloride (P)

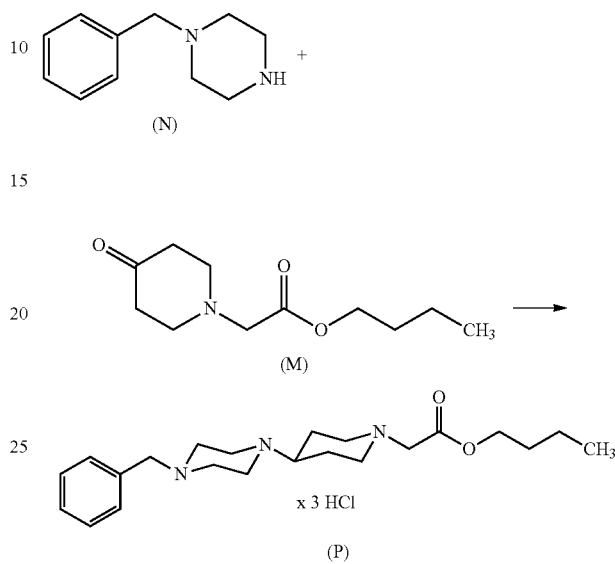

At 21° C., 57.4 g (0.32 mol) 1-benzyl-piperazine (N) were metered into a mixture of 69.5 g (0.33 mol) butyl (4-oxo-piperidin-1-yl)acetate (M), 500 mL tetrahydrofuran and 0.23 L (3.83 mol) acetic acid and rinsed with 200 mL tetrahydrofuran, before the reaction mixture was stirred for three hours at 20° C. Then 109 g (0.49 mol) sodium triacetoxyborohydride was added to the mixture at 20° C. After the addition had ended the mixture was stirred overnight at ambient temperature. Once the reaction of the 1-benzylpiperazine was complete, 300 mL water was metered in and the pH was adjusted to 8.5 with 10M sodium hydroxide solution. After phase separation the organic phase was separated off, dried with MgSO₄ and then evaporated down. The crude product was dissolved in 400 mL EtOH/MeOH [5:1] and combined with 200 mL 5.2 M ethanolic HCL. After cooling to 0° C. and stirring, the product was separated off, washed with cold ethanol and dried.

Yield: 114.9 g (73% of theory)

Example 9

4-(1-piperazinyl)-ethyl 1-piperidinoacetate trihydrochloride (Q)

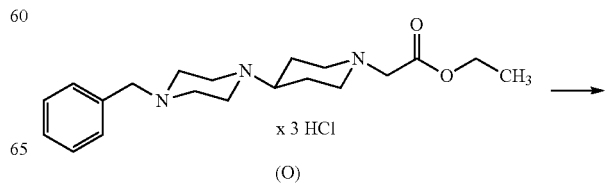

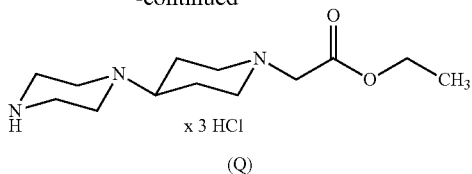

(Q)

6.96 kg (15.3 mol) ethyl [4-(4-benzyl-piperazin-1-yl)piperidin-1-yl]-acetate trihydrochloride (O) were hydrogenated in 66.1 L ethanol and 26.5 L water in the presence of 696 g palladium 10% (50% water) at 50° C. After the reaction was complete the catalyst was filtered off and the residue was washed with a mixture of 7.0 L ethanol and 2.6 L water. Then 111 L acetone were metered in and the mixture was cooled to 0° C., before the product was separated off and dried.

Yield: 5.02 kg (90% of theory)

Example 10

4-(1-piperazinyl)-butyl 1-piperidinoacetate trihydrochloride (R)

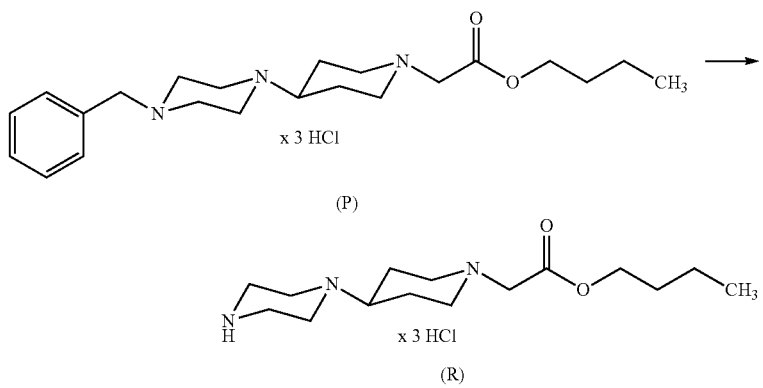

14.6 g (0.03 mol) butyl [4-(4-benzyl-piperazin-1-yl)piperidin-1-yl]-acetate trihydrochloride (P) were hydrogenated in 140 mL methanol and 40 mL water in the presence of 1.45 g palladium/charcoal 10% at 50° C. After the reaction was complete the catalyst was filtered off and the filtrate was evaporated to dryness and digested in 70 mL EtOH.

Yield: 11.2 g (94% of theory)

Example 11

(R)-1-(4-amino-3-chloro-5-trifluoromethyl-benzyl]-2-[4-(1-ethoxycarbonylmethyl-piperidin-4-yl)-piperazin-1-yl]-2-oxy-ethyl 4-(2-oxo-1,2,4,5-tetrahydro-1,3-benzodiazepin-3-yl)-piperidine-1-carboxylate (S)

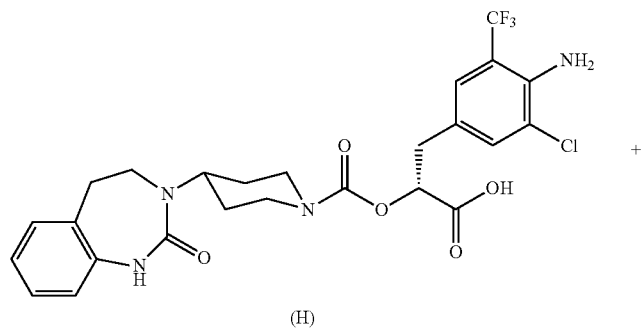

(H)

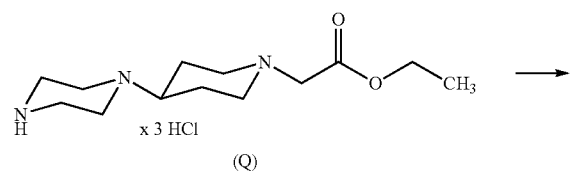

(Q)

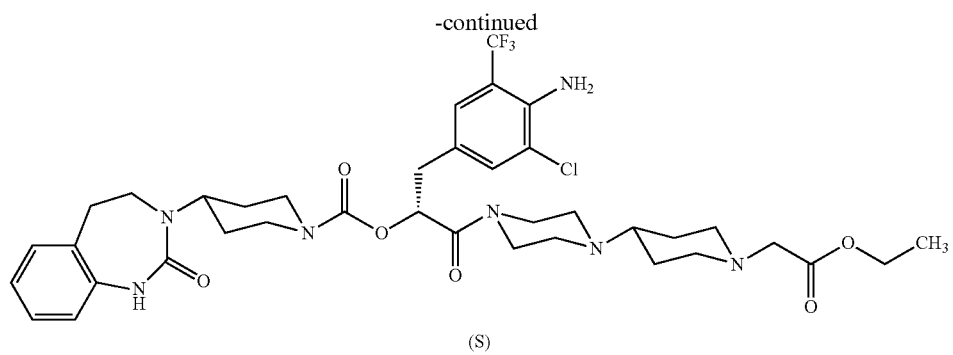

(S)

The suspension of 1.89 kg (3.77 mol) (R)-2-(4-amino-3-chloro-5-trifluoromethyl-phenyl]-1-carboxyethyl 4-(2-oxo-1,2,4,5-tetrahydro-1,3-benzodiazepin-3-yl)-piperidine-1-carboxylate (H), 1.86 kg (4.96 mol) 4-(1-piperazinyl)-ethyl 1-piperidinoacetate trihydrochloride (Q) and 14.5 L of THF was cooled to 0° C., before 3.15 L (22.6 mol) triethylamine were metered in. Then a further 2 L of THF as well as 6.13 L of propanephosphonic anhydride (9.63 mol, 50% in ethyl acetate) were added dropwise. After the addition had ended the reaction mixture was heated to ambient temperature and stirred for at least another hour until total conversion was obtained, before the solvent was eliminated in vacuo. The residue was combined with 20 L ethyl acetate and 14 L water. The pH was adjusted to 7.6 with 10% $Na_2CO_3$ solution. After removal of the organic phase the aqueous phase was re-extracted with 15 L ethyl acetate. The combined organic phases were dried on $Na_2SO_4$ and evaporated to dryness.

Yield: 2.65 kg (82% of theory)

ee value: 99%

Example 12

(R)-1-(4-amino-3-chloro-5-trifluoromethyl-benzyl]-2-[4-(1-ethoxycarbonylmethyl-piperidin-4-yl)-piperazin-1-yl]-2-oxy-butyl 4-(2-oxo-1,2,4,5-tetrahydro-1,3-benzodiazepin-3-yl)-piperidine-1-carboxylate (T)

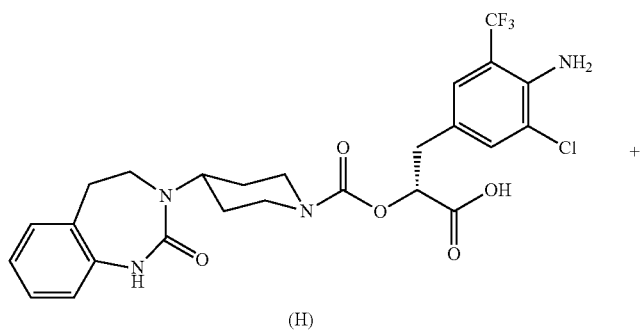

(H)

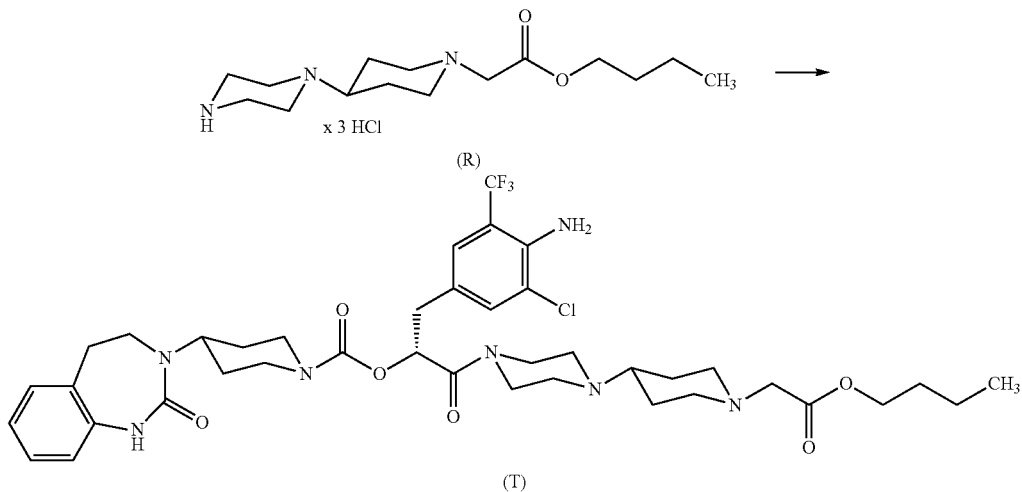

(T)

The mixture of 15 g (27 mmol) (R)-2-(4-amino-3-chloro-5-trifluoromethyl-phenyl]-1-carboxybutyl 4-(2-oxo-1,2,4,5-tetrahydro-1,3-benzodiazepin-3-yl)-piperidine-1-carboxylate (H), 7.66 g (27 mmol) 4-(1-piperazinyl)-butyl 1-piperidinoacetate trihydrochloride (R) and 75 mL THF was cooled to 0° C., before 12.5 mL (89.2 mmol) triethylamine were metered in. Then 32.5 mL propanephosphonic anhydride (54.0 mmol, 50% in ethyl acetate) was added dropwise and the reaction mixture was stirred overnight at ambient temperature. The reaction mixture was [sic] with 100 mL water, 300 mL saturated NaHCO$_3$ solution and 500 mL ethyl acetate. After the separation of the organic phase the aqueous phase was extracted with 250 mL ethyl acetate. The combined organic phases were dried on Na$_2$SO$_4$ and evaporated to dryness.

Yield: 21.1 g (95% of theory)

ee value: 99%

The invention claimed is:

1. A process for preparing a compound of the formula II

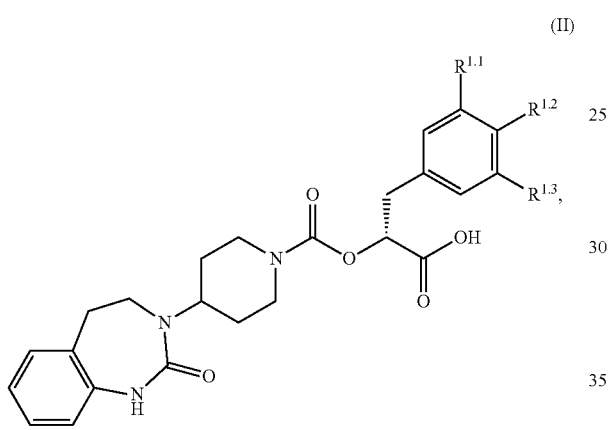

(II)

wherein:

$R^{1.1}$ denotes CH$_3$, CF$_3$, NR$^{1.1.1}$R$^{1.1.2}$ or piperidinyl, $R^{1.1.1}$ denotes H, C$_{1-6}$-alkyl, O-benzyl, O-tert.butyl $R^{1.1.2}$ denotes H, C$_{1-6}$-alkyl, O-benzyl, O-tert.butyl $R^{1.2}$ denotes NR$^{1.2.1}$R$^{1.2.2}$, $R^{1.2.1}$ denotes H, C$_{1-6}$-alkyl, O-benzyl, O-tert.butyl $R^{1.2.2}$ denotes H, C$_{1-6}$-alkyl, O-benzyl, O-tert.butyl and $R^{1.3}$ denotes CH$_3$, CF$_3$, F, Cl or Br, comprising the steps of:

(a) coupling a compound of the formula III

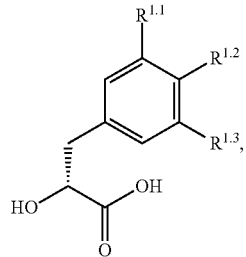

(III)

wherein $R^{1.1}$, $R^{1.2}$ and $R^{1.3}$ are as hereinbefore defined, with a compound of the formula IV

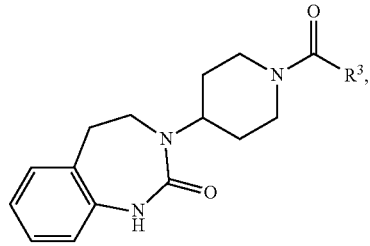

(IV)

wherein R$^3$ denotes an imidazole or triazole group which is bound via a nitrogen atom;

(b) isolating the compound of the formula II obtained in step (a) by crystallisation from a solvent and (c) optionally recrystallising a solid obtained in step (b) from a suitable solvent.

2. The process according to claim 1, wherein the coupling in step (a) is carried out in a solvent and in the presence of a base.

3. The process according to claim 2, wherein the solvent is tert.-amylalcohol, tert.-butanol or tetrahydrofuran.

4. The process according to claim 2, wherein the base is potassium tert.butoxide, sodium-tert.butoxide, lithium-tert.butoxide or sodium-tert.amylate.

5. The process according to claim 1, wherein the solvent in step (b) is water, acetone, ethanol, isopropanol, or n-butyl acetate, or a mixture of two or more of these solvents.

6. A process for preparing a compound of the formula I

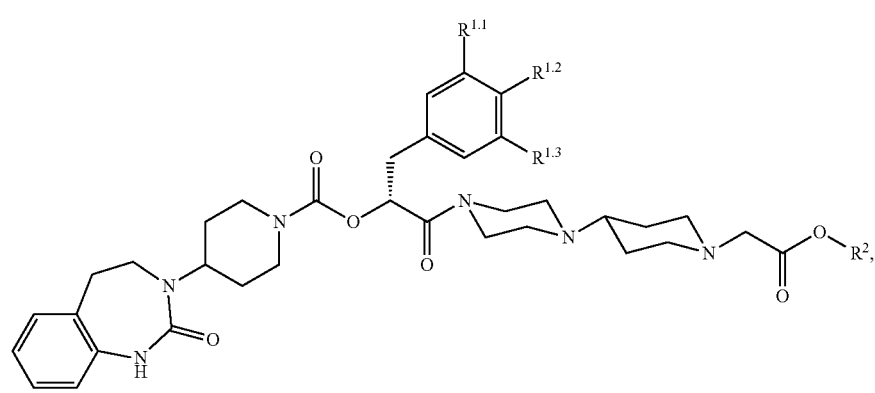

(I)

wherein:

$R^{1.1}$ denotes $CH_3$, $CF_3$, $NR^{1.1.1}R^{1.1.2}$ or piperidinyl, $R^{1.1.1}$ denotes H, $C_{1-6}$-alkyl, O-benzyl, O-tert.butyl $R^{1.1.2}$ denotes H, $C_{1-6}$-alkyl, O-benzyl, O-tert.butyl $R^{1.2}$ denotes $NR^{1.2.1}R^{1.2.2}$, $R^{1.2.1}$ denotes H, $C_{1-6}$-alkyl, O-benzyl, O-tert.butyl $R^{1.2.2}$ denotes H, $C_{1-6}$-alkyl, O-benzyl, O-tert.butyl $R^{1.3}$ denotes $CH_3$, $CF_3$, F, Cl or Br and $R^2$ denotes $C_{1-6}$-alkyl, comprising the steps of:

(a) coupling a compound of the formula III

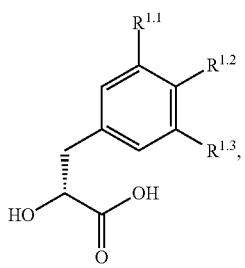

(III)

wherein $R^{1.1}$, $R^{1.2}$ and $R^{1.3}$ are as hereinbefore defined, with a compound of the formula IV

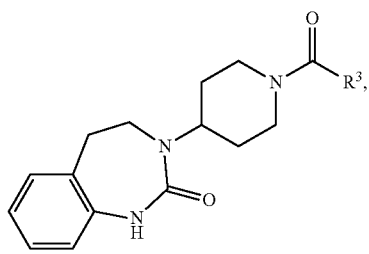

(IV)

wherein $R^3$ denotes an imidazole or triazole group which is bound via a nitrogen atom, to yield a compound of the formula II

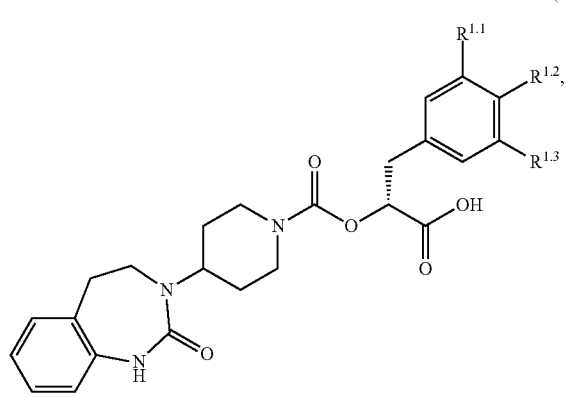

(II)

wherein $R^{1.1}$, $R^{1.2}$ and $R^{1.3}$ are as hereinbefore defined;

(b) reacting the product of the formula II formed in step (a), with a compound of the formula V

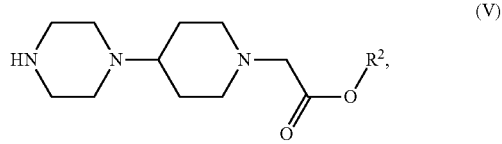

(V)

wherein $R^2$ is as hereinbefore defined; and (c) optionally recrystallising a solid obtained in step (b) from a suitable solvent.

7. The process according to claim 6, wherein the coupling in step (a) is carried out in a polar solvent and in the presence of a strong base.

8. The process according to claim 7, wherein the polar solvent is tert.-amylalcohol, tert.-butanol or tetrahydrofuran.

9. The process according to claim 7, wherein the base is potassium tert.butoxide, sodium-tert.butoxide, lithium-tert.-butoxide or sodium-tert.amylate.

10. The process according to claim 6, wherein the reaction in step (b) is carried out in the presence of an amine and a condensing agent in a polar solvent.

11. The process according to claim 10, wherein the amine is triethylamine, diisopropylethylamine, ethyldiisopropylamine or tributylamine.

12. The process according to claim 10, wherein the condensing agent is propanephosphonic anhydride, dicyclohexylcarbodiimide, carbonyldiimidazole, carbonylditriazole, 2-(1H-benzotriazol-1-yl)-1,1,3,3-tetramethyluronium-tetrafluoroborate, 1-ethyl-3-(3'-dimethylamino-propyl)-carbodiimide and chlorodimethoxy-triazine and is optionally used in the presence of hydroxysuccinimide, hydroxybenzotriazole, p-nitrophenol or pentafluorophenol.

13. The process according to claim 10, wherein the solvent is tetrahydrofuran or ethyl acetate.

14. A process for preparing a compound of the formula III

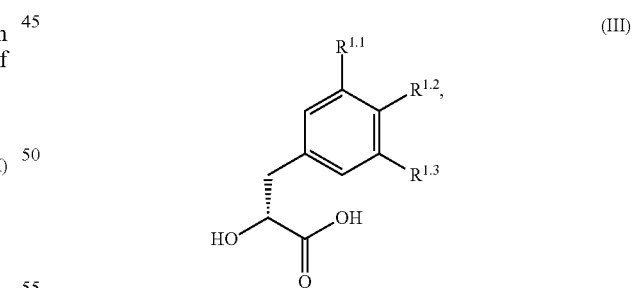

(III)

wherein $R^{1.1}$ denotes $CH_3$, $CF_3$, $NR^{1.1.1}R^{1.1.2}$ or piperidinyl, $R^{1.1.1}$ denotes H, $C_{1-6}$-alkyl, O-benzyl, O-tert.butyl $R^{1.1.2}$ denotes H, $C_{1-6}$-alkyl, O-benzyl, O-tert.butyl $R^{1.2}$ denotes $NR^{1.2.1}R^{1.2.2}$, $R^{1.2.1}$ denotes H, $C_{1-6}$-alkyl, O-benzyl, O-tert.butyl $R^{1.2.2}$ denotes H, $C_{1-6}$-alkyl, O-benzyl, O-tert.butyl and $R^{1.3}$ denotes $CH_3$, $CF_3$, F, Cl or Br, comprising the steps of:

(a) reacting a compound of the formula V

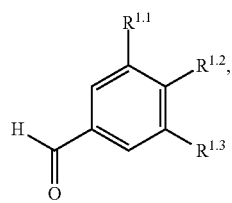

wherein $R^{1.1}$, $R^{1.2}$ and $R^{1.3}$ are as hereinbefore defined, with a compound of the formula VI

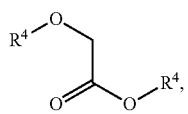

wherein the groups $R^4$ independently of one another denotes a $C_{1-6}$-alkyl group, in a solvent and in the presence of a strong base, to yield a compound of the formula VII

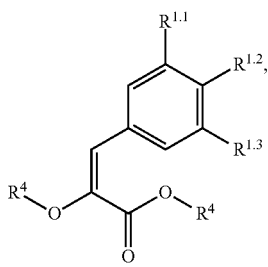

wherein $R^{1.1}$, $R^{1.2}$ and $R^{1.3}$ are as hereinbefore defined and $R^4$ denotes a $C_{1-6}$-alkyl group;

(b) cleaving the ester group of the compound of the formula VII
obtained in step (a), by adding an inorganic base, to yield a compound of the formula VIII

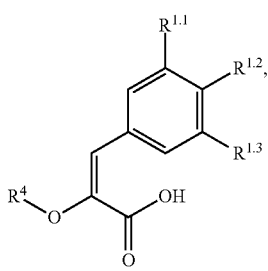

wherein R1.1, R1.2 and R1.3 are as hereinbefore defined and R4 denotes a C1-6-alkyl group;

(c) optionally isolating the compound of the formula VIII obtained in step (b);

(d) cleaving the protective group $R^4$ from the compound of the formula VIII obtained in step (b) or (c) by adding a strong inorganic acid, to yield a compound of the formula IX

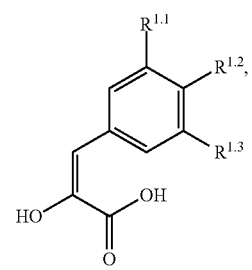

wherein $R^{1.1}$, $R^{1.2}$ and $R^{1.3}$ are as hereinbefore defined;

(e) optionally isolating the compound of the formula IX (IX)

obtained in step (d);

(f) mixing a compound of the formula IX obtained in step (e) with a solvent and reducing the double bond by adding a reducing agent and in the presence of a base, to obtain the compound of the formula III;

(g) isolating the compound of general formula III obtained in step (f) and optionally recrystallising from a solvent.

15. The process according to claim 14, wherein the solvent in step (a) is tert.-butanol, tetrahydrofuran or a mixture of these solvents.

16. The process according to claim 14, wherein the base in step (a) is selected from among potassium tert.butoxide, sodium-tert.butoxide, lithium-tert.butoxide and sodium-tert.amylate.

17. The process according to claim 14, wherein the base in step (b) is selected from among lithium hydroxide, sodium hydroxide and potassium hydroxide.

18. The process according to claim 14, wherein the inorganic acid in step (d) is selected from among hydrochloric acid, hydrobromic acid, hydriodic acid and sulphuric acid.

19. The process according to claim 14, wherein the solvent in step (f) is selected from among n-butyl acetate, isopropyl acetate, ethyl acetate and tetrahydrofuran.

20. The process according to claim 14, wherein the base in step (f) is selected from among triethylamine, diisopropylethylamine and pyridine.

21. The process according to claim 14, wherein the reducing agent in step (f) is selected from among diisopinocampheyl boron chloride, β-chlorodiisopinocampheylborane, Alpine borane and methyl-CBS-oxazaborolidine.

22. The process according to claim 14, wherein the solvent in step (g) is selected from among n-butyl acetate, isopropyl acetate, ethyl acetate and tetrahydrofuran.

23. A process for preparing a compound of the formula V

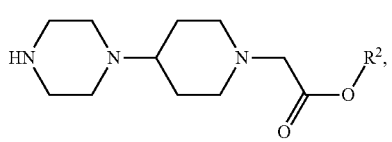

wherein
R$^2$ denotes C$_{1-6}$-alkyl,
comprising the steps of:
(a) reacting piperidone-4-hydrate-hydrochloride with a chloroacetic acid ester of the formula X

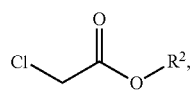

wherein R$^2$ denotes a C$_{1-6}$-alkyl group, in a solvent and in the presence of a base, to yield a compound of the formula XI

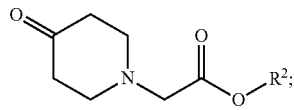

(b) coupling the compound of formula XI

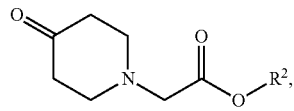

obtained in step (a), wherein R$^2$ is as hereinbefore defined, with 1-benzylpiperidine in a solvent and with the addition of a reducing agent, to yield a compound of the formula XII

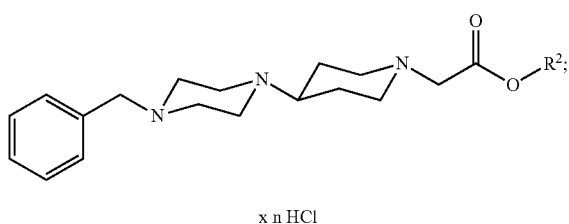

x n HCl (c) reacting the compound of the formula XII obtained in step (b), wherein R$^2$ is as hereinbefore defined and n denotes the number 0, with hydrochloric acid and in a solvent, in order to prepare a compound of the formula XII

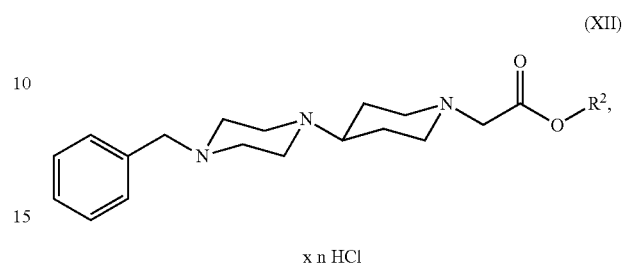

x n HCl wherein R$^2$ is as hereinbefore defined and n denotes one of the numbers 1, 2 or 3; and
(d) cleaving the benzyl protective group from the compound of formula XII, obtained in step (c), wherein R$^2$ is as hereinbefore defined and n denotes one of the numbers 1, 2 or 3, in a solvent and in the presence of a catalyst, to yield a compound of the formula XIII

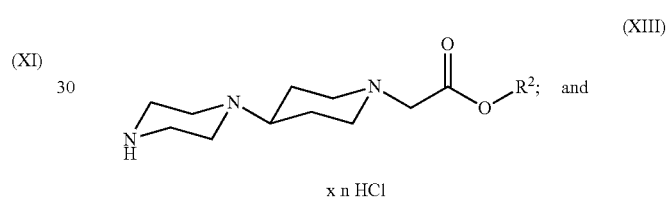

x n HCl (e) isolating a the compound of the general formula XIII prepared in step (d), wherein R$^2$ is as hereinbefore defined and n denotes one of the numbers 1, 2 or 3.

24. The process according to claim 23, wherein the solvent in step (a) is acetone, acetonitrile, tert-butylmethylether, N,N-dimethylacetamide, dimethylformamide, dimethylsulphoxide, pyridine or N-methylpyrrolidone.

25. The process according to claim 23, wherein the base in step (a) is sodium carbonate, potassium carbonate, sodium hydride or potassium hydride.

26. The process according to claim 23, wherein the solvent in step (b) is tert-butylmethylether, tetrahydrofuran, toluene or 2-methyltetrahydrofuran.

27. The process according to claim 23, wherein the reducing agent in step (b) is sodium borohydride or sodium-triacetoxyborohydride.

28. The process according to claim 23, wherein the solvent in step (c) is methanol, ethanol or isopropanol.

29. The process according to claim 23, wherein the solvent in step (d) is methanol, ethanol, propanol, tert-butanol, water, acetone, tetrahydrofuran, dimethylformamide or a mixture of these solvents.

30. The process according to claim 23, wherein the catalyst in step (d) is palladium/charcoal or palladium hydroxide/charcoal.

* * * * *